United States Patent
Thompson et al.

(10) Patent No.: US 6,562,000 B2
(45) Date of Patent: May 13, 2003

(54) SINGLE-USE THERAPEUTIC SUBSTANCE DELIVERY DEVICE WITH INFUSION RATE CONTROL

(75) Inventors: David L. Thompson, Andover, MN (US); Michael F. Mattes, Chandler; Lary R. Larson, Gold Canyon, both of AZ (US); Kenneth T. Heruth, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 48 days.

(21) Appl. No.: 09/776,471

(22) Filed: Feb. 2, 2001

(65) Prior Publication Data

US 2002/0107472 A1 Aug. 8, 2002

(51) Int. Cl.$^7$ ............................................... A61B 17/39
(52) U.S. Cl. ............................ 604/48; 604/67; 604/132
(58) Field of Search ........................... 604/509, 48, 67, 604/132; 606/545

(56) References Cited

U.S. PATENT DOCUMENTS

| | | |
|---|---|---|
| 4,447,224 A | 5/1984 | DeCant, Jr. et al. |
| 4,525,165 A | 6/1985 | Fischell |

(List continued on next page.)

FOREIGN PATENT DOCUMENTS

| | | |
|---|---|---|
| EP | 0 300 552 A1 | 1/1989 |
| EP | 0 344 895 A2 | 12/1989 |
| EP | 0 564 321 A2 | 3/1993 |
| EP | 0 892 419 A2 | 1/1999 |
| EP | 0 951 916 A2 | 10/1999 |
| JP | 05220222 | 8/1993 |
| WO | WO 98/23869 | 6/1998 |

OTHER PUBLICATIONS

"microID™ 125 KhZ rfid system Design Guide", *Microchip Technology Inc.*, pp. 1–46, (Dec. 1998).

"Introducing The Microstamp Engine™", *Micron Communications Inc.* 2 pgs., (1997).

(List continued on next page.)

*Primary Examiner*—Philippe Derakshani
(74) *Attorney, Agent, or Firm*—Stephen W. Bauer; Eric R. Waldkoetter; Thomas G. Berry

(57) ABSTRACT

A medical device known as a therapeutic substance delivery device is configured to with an infusion rate control to deliver a therapeutic substance such as pharmaceutical compositions, genetic materials, and biologics to treat a variety of medical conditions such as pain, spasticity, cancer, and other diseases in humans and other animals. The therapeutic substance delivery device can be configured as a single-use device that is versatile, small, inexpensive, and has many other improvements. The single-use device has a Micro Electro Mechanical System (MEMS) flow restriction with a variable infusion rate. The MEMS flow restriction is fluidly coupled to a reservoir outlet to receive therapeutic substance dispensed from the single-use reservoir at the reservoir rate and restrict the therapeutic substance flow to a desired infusion rate. The single-use reservoir is configured for controlled collapse to dispense therapeutic substance from the reservoir at a reservoir rate through a reservoir outlet. The therapeutic substance delivery device can also be configured as a shrink polymer delivery device that is also versatile, small, inexpensive, and has many other improvements. A flow restriction is fluidly coupled to the shrink polymer reservoir outlet to receive therapeutic substance dispensed from the reservoir at the reservoir rate and restrict the therapeutic substance flow to an infusion rate. Many embodiments of the therapeutic substance delivery device with infusion rate control and its methods of operation are possible.

37 Claims, 11 Drawing Sheets

U.S. PATENT DOCUMENTS

| | | |
|---|---|---|
| 4,772,263 A | 9/1988 | Dorman et al. |
| 4,871,351 A | 10/1989 | Feingold |
| 4,931,050 A | 6/1990 | Idriss |
| 5,045,064 A | 9/1991 | Idriss |
| 5,061,243 A | 10/1991 | Winchell et al. |
| 5,163,920 A | 11/1992 | Olive |
| 5,188,260 A | 2/1993 | Bettinger |
| 5,252,962 A | 10/1993 | Urbas et al. |
| 5,368,588 A | 11/1994 | Bettinger |
| 5,423,334 A | 6/1995 | Jordan |
| 5,427,585 A | 6/1995 | Bettinger |
| 5,448,110 A | 9/1995 | Tuttle et al. |
| 5,457,447 A | 10/1995 | Ghaem et al. |
| 5,474,527 A | 12/1995 | Bettinger |
| 5,552,197 A | 9/1996 | Bettinger |
| 5,616,127 A | 4/1997 | Smith |
| 5,702,618 A | 12/1997 | Saaski et al. |
| 5,797,898 A | 8/1998 | Santini, Jr. et al. |
| 5,820,589 A | 10/1998 | Torgerson et al. |
| 5,833,603 A | 11/1998 | Kovacs et al. |
| 5,897,530 A | 4/1999 | Jackson |
| 5,944,717 A * | 8/1999 | Lee et al. .................. 606/545 |
| 6,183,441 B1 | 2/2001 | Kriesel et al. |
| 6,197,013 B1 * | 6/2001 | Reed et al. ................. 604/509 |

OTHER PUBLICATIONS

"High Reliability Long–Term Lubricators Based On Heat–Shrink Polymers", *The Technology Partnership*, 2 pgs., (Sep. 1994).

"Controlled Stepwise Motion in Polysilicon Microstructures", *Journal of Microelectromechnical Systems,* vol. 2, No. 3, pp. 106–110 (Sep. 1993).

"Digital RF/ID Enhances GPS", *Micron Communications, Inc.,* pp. 406–411 (Date Unknown).

"ALZET® osmotic Pumps, A General Description", pp. 2–5 (Date Unknown).

* cited by examiner

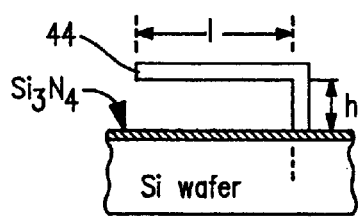
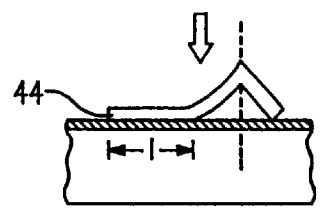
FIG. 8a     FIG. 8b
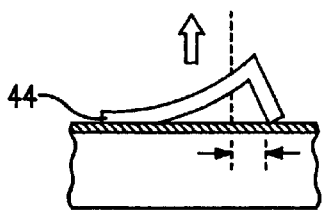
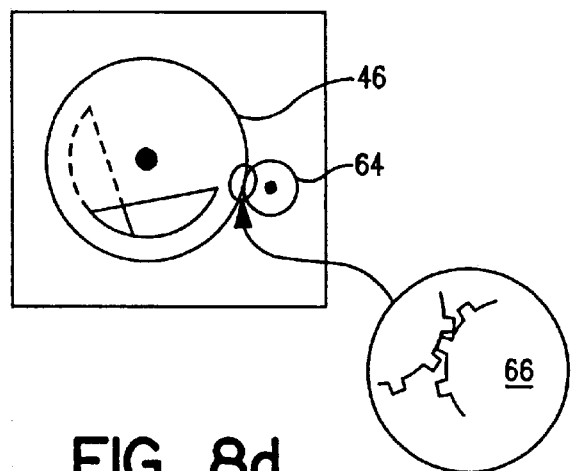
FIG. 8c     FIG. 8d
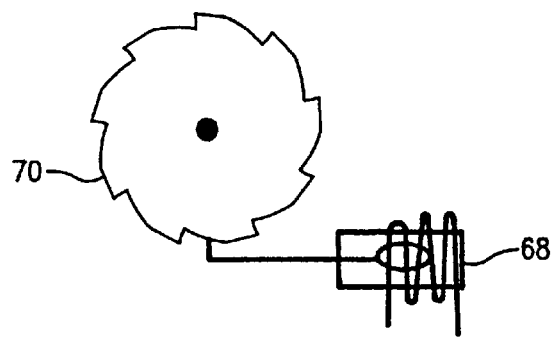
FIG. 8e

SINGLE-USE THERAPEUTIC SUBSTANCE DELIVERY DEVICE WITH INFUSION RATE CONTROL

CROSS REFERENCE

The present application is related to the following copending application entitled "Variable Infusion Rate Catheter" by inventors Thompson et al. Ser. No 09/776,436 which is not admitted as prior art with respect to the present invention by its mention in this cross reference section.

BACKGROUND OF THE INVENTION

This disclosure relates to a medical device and more particularly to a therapeutic substance delivery device.

The medical device industry produces a wide variety of electronic and mechanical devices for treating patient medical conditions. Depending upon medical condition, medical devices can surgically implanted or connected externally to the patient receiving treatment. Clinicians use medical devices alone or in combination with therapeutic substance therapies and surgery to treat patient medical conditions. For some medical conditions, medical devices provide the best, and sometimes the only, therapy to restore an individual to a more healthful condition and a fuller life. One type of medical device is therapeutic substance delivery device.

Therapeutic substance delivery devices are also known as drug pumps and drug delivery devices. Therapeutic substance delivery devices are typically used to treat a condition that responds to a therapeutic substance delivered directly to an infusion site in the body rather than being ingested. Therapeutic substance delivery devices are used to treat conditions such as pain, spasticity, cancer, infections, gene abnormalities, and the like. Therapeutic substance delivery devices can be external to a patient with an infusion catheter inserted into the patient to deliver the therapeutic substance to an infusion site. Therapeutic substance delivery devices can also be implanted typically subcutaneously into a patient typically with a catheter that is also implanted to deliver therapeutic substance to an infusion site. Some therapeutic substance delivery devices are refillable such as the SynchroMed® Infusion System available from Medtronic, Inc. Other therapeutic substance delivery devices are intended as single-use devices.

Single-use therapeutic substance delivery devices are typically used in therapies where it is desirable to use a small device, an inexpensive device, or both. Single-use devices are typically configured with a preset infusion rate such as an osmotic pump available from DURECT Corp. as shown in their brochure titled "ALZETS® Osmotic Pumps, A General Description." Other single-use therapeutic substance delivery devices use the collapsing reservoir alone to control the device infusion rate such as disclosed in U.S. Pat. No. 5,368,588 "Parenteral Fluid Medication Reservoir Pump" by Bettinger (Nov. 29, 1994).

For the foregoing reasons, there is a need for a single-use therapeutic substance delivery device that has a variable infusion rate control and a shrink-polymer therapeutic substance delivery device with an infusion control to provide single-use therapeutic substance delivery devices that are versatile, small, inexpensive, and have many other improvements.

SUMMARY OF THE INVENTION

A single-use therapeutic substance delivery device with infusion rate control is versatile, small, inexpensive, and has many other improvements. The therapeutic substance delivery device has a Micro Electro Mechanical System (MEMS) flow restriction with a variable infusion rate. The MEMS flow restriction is fluidly coupled to a reservoir outlet to receive therapeutic substance dispensed from the single-use reservoir at the reservoir rate and restrict the therapeutic substance flow to a desired infusion rate. The single-use reservoir is configured for controlled collapsing to dispense therapeutic substance from the reservoir at a reservoir rate through a reservoir outlet. Many embodiments of the single-use therapeutic substance delivery device with infusion rate control and its methods of operation are possible.

A single-use shrink-polymer therapeutic substance delivery device is versatile, small, inexpensive, and has many other improvements. A flow restriction is fluidly coupled to the shrink polymer reservoir outlet to receive therapeutic substance dispensed from the reservoir at the reservoir rate and restrict the therapeutic substance flow to an infusion rate. The shrink polymer reservoir configured for controlled collapsing to dispense therapeutic substance from the reservoir at a reservoir rate through a reservoir outlet. Many embodiments of the single-use shrink-polymer therapeutic substance delivery device with infusion rate control and its methods of operation are possible.

BRIEF DESCRIPTION OF THE DRAWINGS

FIGS. 8a–8c show views of a stepwise actuator for a MEMS flow restriction embodiment;

FIG. 8d shows a Direct Current (DC) motor actuator for a MEMS flow restriction embodiment;

FIG. 8e shows a heat engine actuator for a MEMS flow restriction embodiment;

DETAILED DESCRIPTION OF THE PREFERRED EMBODIMENTS

Figure 1:
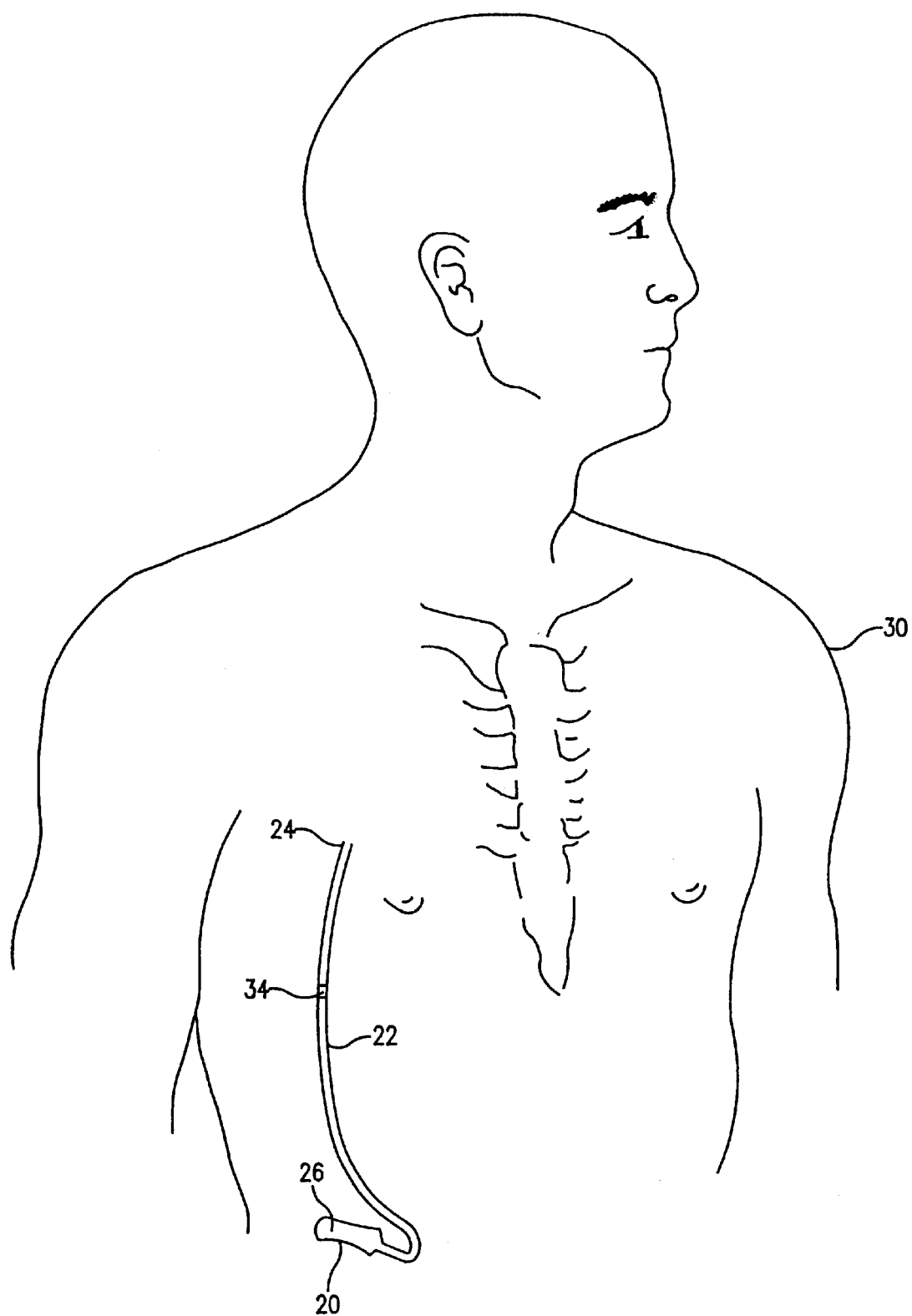
FIG. 1 shows the environment of a therapeutic substance delivery device embodiment.

FIG. 1 shows the environment of a medical device known as therapeutic substance delivery device embodiment. The therapeutic substance delivery device 20 can be used for a wide variety of therapies such as pain, spasticity, cancer, and other medical conditions. For implantable versions of the therapeutic substance delivery device 20, implantation is typically done by a clinician such as a surgeon in a sterile perutaneous or surgical procedure performed under local, regional, or general anesthesia. In some embodiments, before implanting the therapeutic substance delivery device 20, a catheter 22 can be implanted with the distal end 24 positioned at the desired therapeutic substance delivery site and the proximal end tunneled to the location where the therapeutic substance delivery device 20 is to be implanted. The implantable therapeutic substance delivery device 20 is generally implanted subcutaneously about 2.5 cm (1.0 inch) beneath the skin where there is sufficient subcutaneous tissue to support the implanted system. Once the therapeutic substance delivery device 20 is subcutaneously implanted into the patent the opening used to insert the therapeutic substance delivery device 20 is closed. When the therapeutic substance delivery device 20 is surgically implanted, the incision can be sutured closed.

The therapeutic substance delivery device 20 operates to infuse a therapeutic substance 26 at a programmed rate into a patient 30. The therapeutic substance 26 is a product or substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances are substances intended to have a therapeutic effect yet are not easily classified such as saline solution, fluoroscopy agents, and the like.

Figure 2:
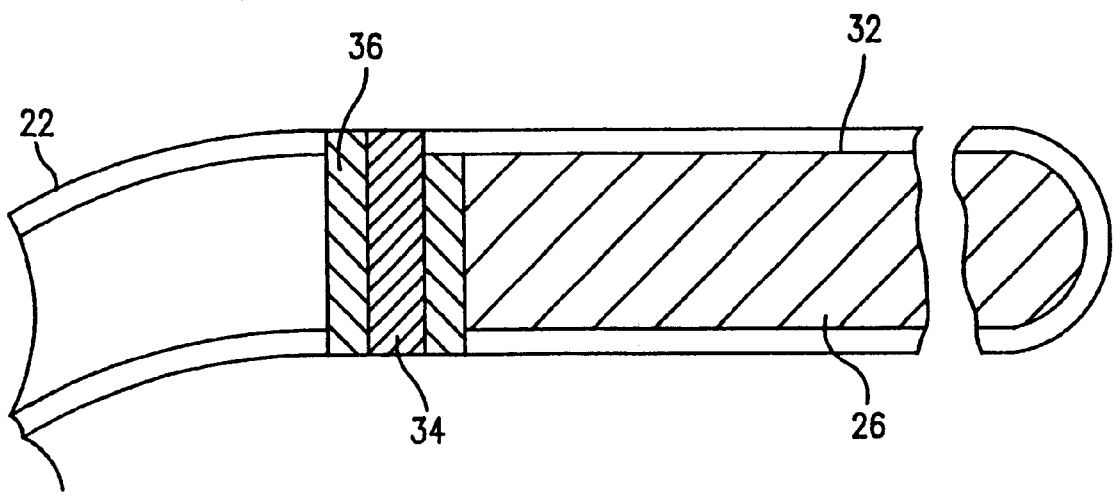
FIG. 2 shows a single-use therapeutic substance delivery device embodiment.
Figure 3:
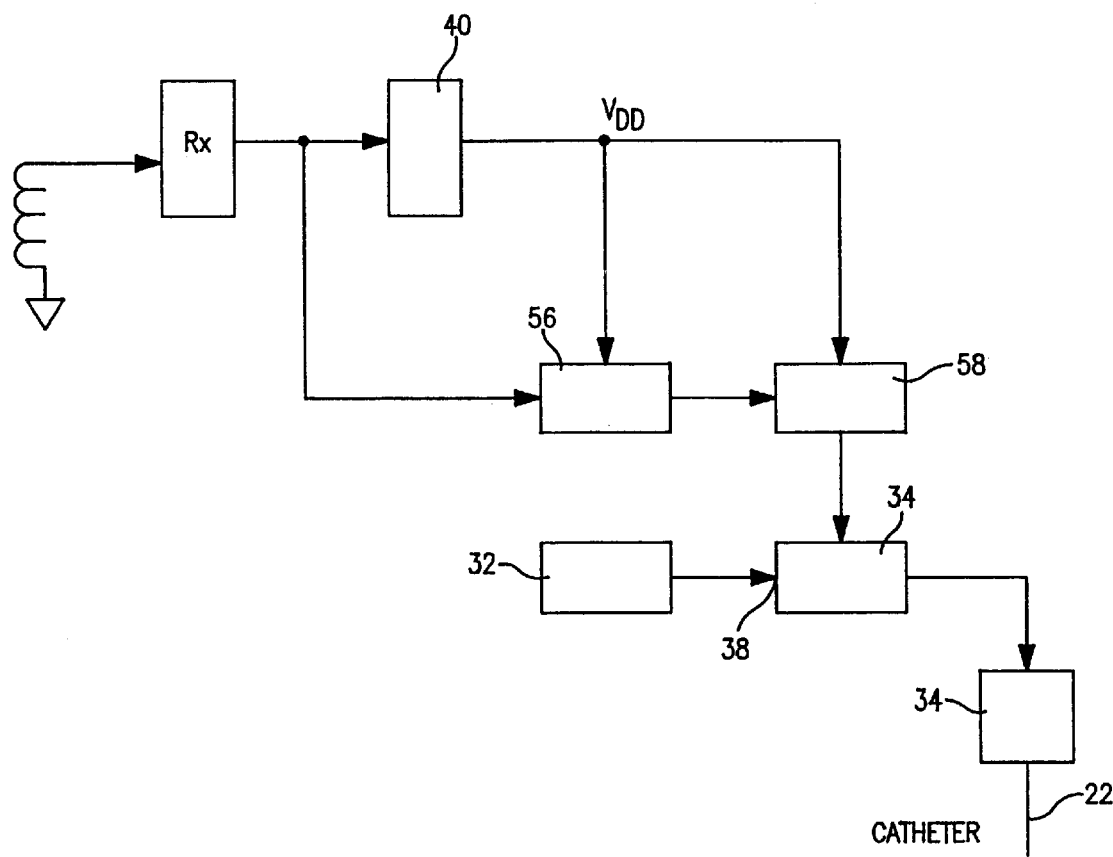
FIG. 3 shows an electrical circuit schematic for a Micro Electro Mechanical System (MEMS) flow restriction embodiment.

FIG. 2 shows a single-use therapeutic substance delivery device 20 embodiment, and FIG. 3 shows a schematic for a therapeutic substance delivery device 20 with a Micro Electro Mechanical System (MEMS) infusion control embodiment. A single-use therapeutic substance delivery device 20 with infusion rate control comprises a single-use reservoir 32 and a MEMS flow restrictor 34. The single use reservoir 32 is configured for controlled collapsing to dispense therapeutic substance 26 from the reservoir 32 at a reservoir rate through a reservoir outlet 36. The single-use reservoir 26 is a reservoir that provides its own pressurization such as a shrink polymer reservoir, and elastomeric bladder, and the like. Some embodiments of the single-use therapeutic substance delivery device 20 can be configured without a catheter 22 to delivery therapeutic substance 26 at an infusion site near the MEMS flow restrictor 34. Other embodiments of the single-use therapeutic substance delivery device 20 can be configured with a catheter 22 to permit delivery of therapeutic substance 26 at an infusion site remotely located from the MEMS flow restrictor 34.

Figure 4:
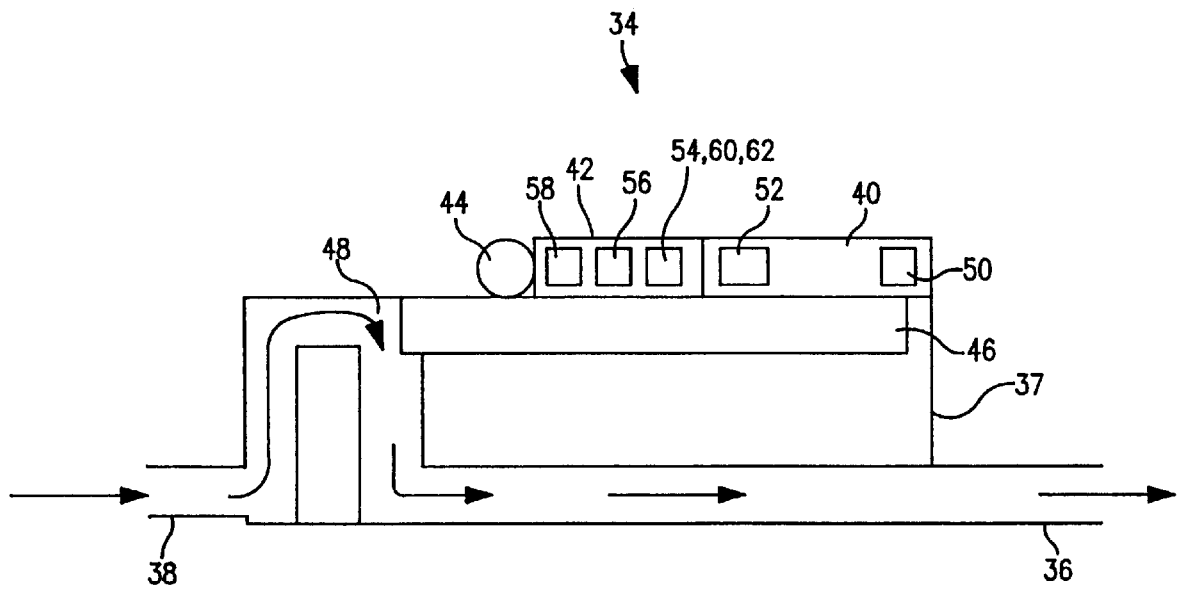
FIG. 4 shows a block diagram of a MEMS flow restriction embodiment.
Figure 5:
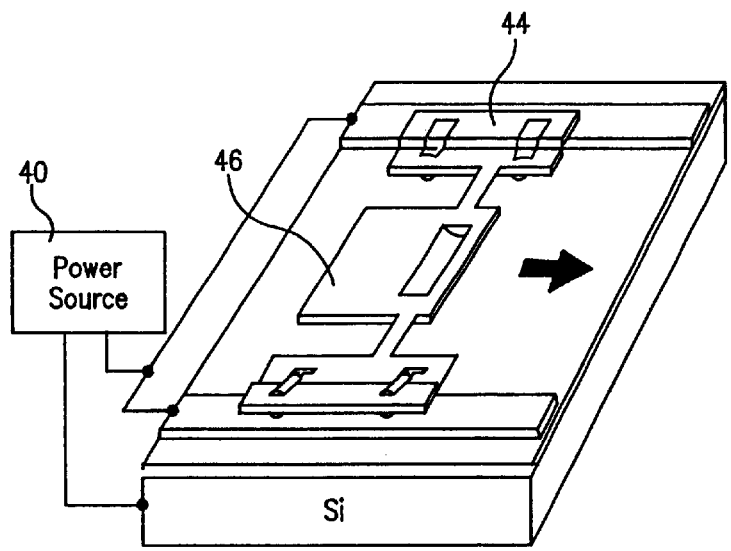
FIG. 5 shows an isometric view of a MEMS flow restriction embodiment.

FIG. 4 shows a MEMS flow restriction 34 block diagram embodiment, and FIG. 5 shows an isometric view of a MEMS flow restriction 34 embodiment. A MEMS flow restrictor 34 is fluidly coupled to the reservoir outlet 36 to receive therapeutic substance 26 dispensed from the reservoir 32 at the reservoir rate. The MEMS flow restriction 34 restricts the therapeutic substance 26 flow to an infusion rate. The MEMS flow restriction 34 is comprised of a substrate 37, a MEMS inlet 38, a MEMS outlet 36, a passive power source 40, electronics 42, an actuator 44, and a valve 46. The flow restriction 48 provides a structure to restrict therapeutic substance 26 flow that can be varied with a valve 46 such as a continuous path, a plurality of restriction outlets, and the like. MEMS 34 components such as the MEMS inlet 38 and MEMS outlet 36 can be assembled using glass frit bonding, electrostatic anodic bonding, and the like. MEMS 34 components that may contact the therapeutic substance 26 can be coated with a substance to improve chemical compatibility with the therapeutic substance and with body tissues such as titanium, platinum, gold, parylene, and the like. The MEMS substrate 37 can be cut in shape appropriate for the application such as round, rectangular, square, and the like with a laser cutter or wafer scribe saws. When configured in a round shape, the MEMS 34 is particularly well suited for use in a catheter 22 or single-use reservoir outlet 36.

The passive power source 40 is carried on the substrate 37 and comprises an antenna coil 50 and modulation circuitry 52. The passive power source 40 is capable of supplying power upon being energized by a Radio Frequency source. In one embodiment, the passive power source is operates according to Radio Frequency Identification (RFID) principals such as described in the Microchip Technology Inc., microID™ 125 kHz RFID System Design Guide (1998), U.S. Pat. No. 5,833,603 "Implantable Biosensing Transponder" by Kovacs et al., and U.S. Pat. No. 5,252,962 "System Monitoring Programmable Implantable Transponder" by Urbas et al. The RF signal is transmitted by a device such as an interrogator or a clinician's programmer configured to transmit the RF signal. The RF signal can be generated at any acceptable frequency such as 125 KHz, 13.56 MHz, 2.4 GHz, and the like. The RF signal field varies in voltage from the very near field of about 200 $V_{pp}$ to the far field of about 5 $V_{pp}$. The RF signal contacts a carrier signal at the selected frequency and a data signal modulated on this carrier signal with modulation techniques such as amplitude modulation, frequency modulation, frequency shift keying, phase modulation, phase shift keying, and the like. When the RF signal passes through the antenna coil 50, an Alternating Current (AC) voltage is generated across the antenna coil 50 and the antenna coil 50 receives the data signal. In addition to the passive power source 40, the MEMS flow restriction 34 could be configured similarly to that disclosed in U.S. Pat. No. 5,702,618 by Saaski and operated as described in Akiyama "Controlled Stepwise Motion In Polysilicon 5Microstructures" IEEE Journal of Microelectromechanical Systems, Vol. 2, No. 3 (Sep. 1993). The MEMS flow restriction 34 can also be configured as described below.

The electronics 42 are carried on the substrate 37 and coupled to the passive power source 40. The electronic 42 include a rectifier 54, receiver circuitry 56, and control circuitry 58. The rectifier 54 rectifies the AC voltage generated across the antenna coil 50 to power the MEMS 34. The rectified power available to the MEMS 34 depends upon how the passive power source 40 is configured and can range from a voltage from less than about 2 VDC to about 10 VDC and current from less than about 5 µA to about 50 mA. The receiver 56 is configured for the type of modulation being used to receive the data signal and produces an information signal. The control circuitry 58 converts the information signal into a control signal that is configured to operate the actuator. In some embodiments, the electronics 42 can be configured with a transmitter 60 to transmit selected information from nonvolatile memory 62 through the antenna coil 50 to the interrogator. The transmitter 62 can be a shunt transistor placed across the antenna coil 50 that is operated to cause amplitude fluctuations in the interrogator's RF carrier amplitude. The backscattered signal can be used to provide information about the MEMS 34 such as the MEMS 34 model number, MEMS 34 serial number, programmed infusion rate, and the like.

The actuator 44 is carried on the substrate and coupled to the electronics 42. The actuator 44 is a device that moves to operate the valve 46 in response to the control signal such as a stepwise rotor, a heat motor, a Direct Current (DC) motor, and the like. The heat motor contains a material that changes shape or volume in response to heat such as a memory metal, wax, and the like. In a memory metal embodiment, the memory metal such as nitanol can be formed in the shape of a bubble that changes shape in response to heat. In some embodiments, the actuator 44 can include a mechanical coupling between the actuator and the valve such as a ratchet wheel to couple the heat motor to the valve, a gear to couple the DC motor to the valve, and the like.

Figure 9A:
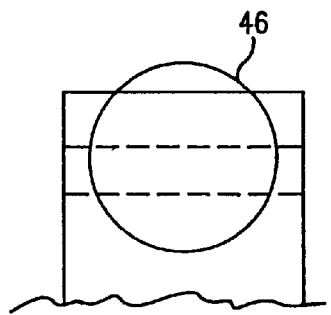
FIGS. 9a–9c show valve configurations for a MEMS flow restriction embodiment.
Figure 9B:
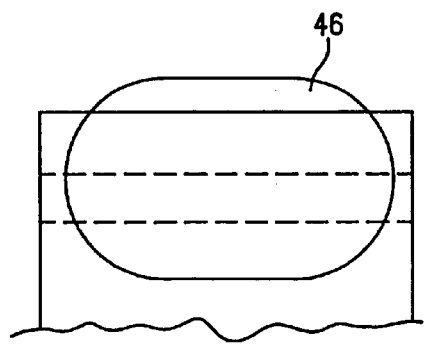
Figure 9C:
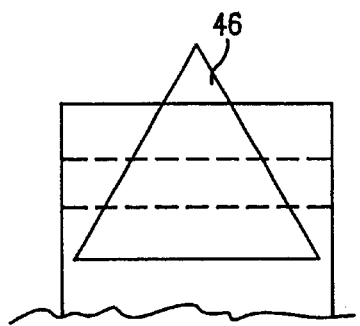

The valve 46 is movably coupled to the substrate 37 to selectively engage the flow restriction 48. The valve 46 can take many different forms to adjust the flow restriction 48 such as a shutter, a moveable plate, a rotatable restrictor, and the like. When the valve is a moveable plate or shutter, the valve can be configured in a variety of shapes such as a circle, oval, triangle, and the like (FIGS. 9a–9c). The valve 46 is operated by the actuator 44 to selectively adjust the flow restriction 48 to create the infusion rate.

Figure 6A:
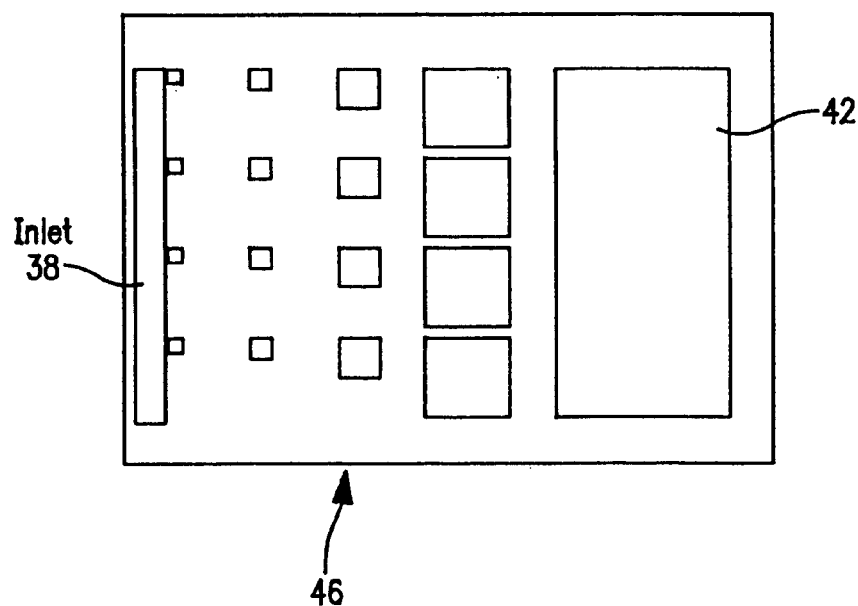
FIG. 6a shows a top view of a MEMS flow restriction having multiple outlets embodiment.
Figure 6B:
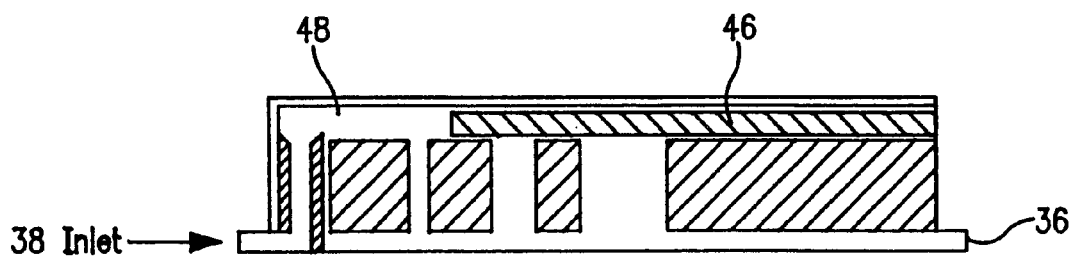
FIG. 6b shows a side view of the MEMS in FIG. 4a embodiment.
Figure 7A:
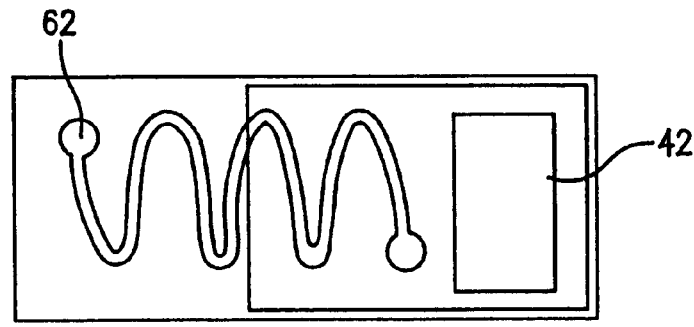
FIG. 7a shows a top view of a MEMS flow restriction having a continuous flow path embodiment.
Figure 7B:
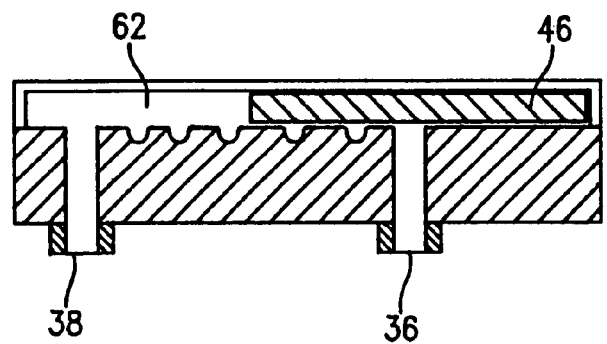
FIG. 7b shows a side view of the MEMS in FIG. 4a embodiment.

Many different embodiments of MEMS flow restriction 34 components are possible. FIGS. 6a–6b show an embodiment using multiple outlets that are opened, partially opened, and closed by the actuator. In another version of this embodiment, the multiple outlets are covered with a membrane. The infusion rate is programmed by the actuator 44 breaking or blowing the membrane covering selected outlets. A limitation in using membrane as the valve is that once the membrane is opened over a selected outlet that outlet cannot be closed, so reprogramming is limited to increasing the infusion rate. FIGS. 7a–7b show an embodiment of the MEMS flow restriction 34 with a continuous flow path 62. FIGS. 8a–8c show an actuator 44 embodiment using controlled stepwise motion. The stepwise motion is created by applying a voltage across the L shaped member and the substrate causing the L shaped member to be electrostatically attracted to the substrate. When the voltage is no longer applied, the L shaped member relaxes, and the L shaped member has moved forward delta x. FIG. 8d shows a DC motor 64 that can operate bi-directionally engaging a gear 66 that rotates a rotary valve 46 to adjust the infusion rate. FIG. 8e shows a heat engine 68 engaging a ratchet wheel 70 that can rotate a rotary valve 46 such as shown in FIG. 8d to adjust the infusion rate. FIGS. 9a–9c show various shapes for shutter type valves 46. The shutters can be shaped to change the infusion rate with movement in a linear or nonlinear manner.

In an alternative embodiment, a MEMS flow restriction 34 can be placed downstream from the reservoir 32 on the catheter 22 whether or not the reservoir 32 has a flow restriction 48. In another embodiment, two or more MEMS flow restrictions 34 can be placed downstream from the reservoir 32 on one or more catheters 22 whether or not the reservoir 32 has a flow restriction. When the MEMS flow restriction 34 is placed serially on a catheter 22, different infusion outlets can have different infusion rates. When more than one MEMS flow restriction 34 is placed on two or more branches of a catheter 22, the different catheter branches can have different infusion rates.

Figure 10:
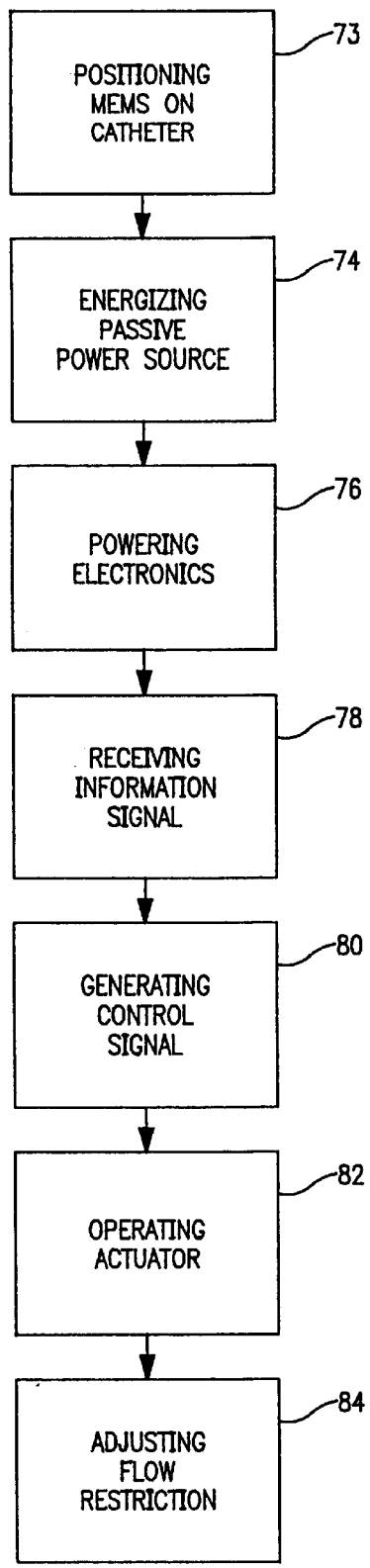
FIG. 10 shows a shrink polymer therapeutic substance delivery device embodiment.

FIG. 10 shows a method for operating the MEMS flow restriction 34. The MEMS flow restriction 34 operates according to the following method. A passive power supply is energizing 74 with a radio frequency signal. The energized passive power supply powers 76 the electronics. The powered electronics receive 78 an information signal modulated on the radio frequency signal. The information signal contains at least one instruction for the MEMS flow restriction such as change the infusion rate, identify the MEMS flow restriction by model and serial number, and the like. The electronics generate 80 a control signal that is response to the information signal. The control signal is configured to drive the actuator used in the MEMS flow control embodiment. The actuator operates 82 in response to the control signal. The motion of the actuator is used to adjust 84 the valve to adjust the flow restriction to an infusion rate. In some embodiments, the method can also include transmitting a status signal with the electronics such as the currently programmed infusion rate.

Figure 11:
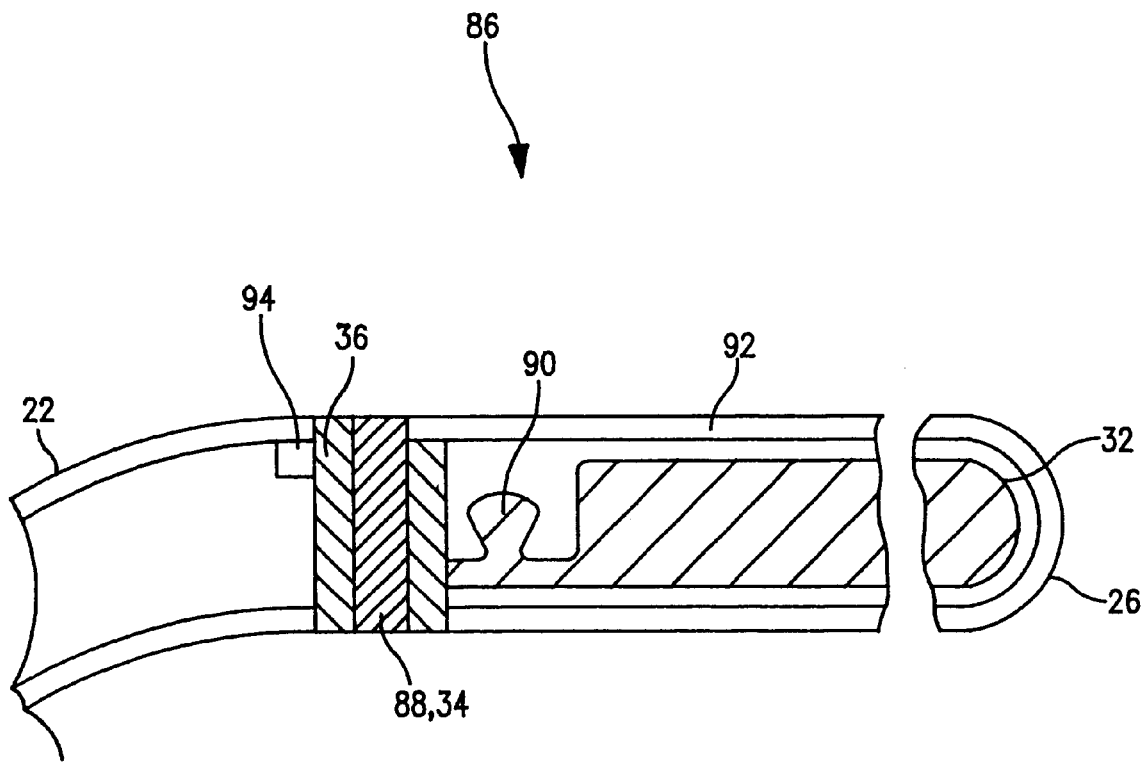
FIG. 11 shows a flowchart of a method for operating a MEMS flow restriction embodiment; and, FIG. 12 shows a flowchart of a method for delivering a therapeutic substance from a single-use reservoir with infusion rate control embodiment.

FIG. 11 shows a shrink polymer therapeutic substance delivery device 86 embodiment. The shrink polymer therapeutic substance delivery device 86 with infusion rate control comprises a shrink polymer reservoir 32 and a flow restriction 88. The shrink polymer therapeutic substance delivery device 86 can be configured to be implanted. The shrink polymer therapeutic substance delivery device 86 can be configured for percutaneous insertion into a patient. Some embodiments of the shrink polymer therapeutic substance delivery device 86 can be configured without a catheter 22 to delivery therapeutic substance 26 at an infusion site near the flow restrictor 88. Other embodiments of the shrink polymer therapeutic substance delivery device 86 can be configured with a catheter 22 to permit delivery of therapeutic substance 26 at an infusion site remotely located from the flow restrictor 88.

The shrink polymer reservoir 32 is configured for controlled collapsing to dispense therapeutic substance 26 from the reservoir 32 at a reservoir rate through a reservoir outlet. The shrink polymer reservoir 32 serves as a means for containing a therapeutic substance 26 that collapses in a controlled manner to dispense therapeutic substance 26. The shrink polymer reservoir 32 typically collapses substantially linearly with time with tolerances such as in the range from about ±1% to about ±5%. The shrink polymer can be configured to begin its substantially linear collapse upon reaching a certain temperature. For example, the shrink polymer reservoir 32 can be configured to be stable and not collapse at temperature below about 26.7° C. (80° F.) and configured to begin collapsing at temperatures above 35° C. (95° F.) such as upon implantation in a body. The shrink polymer reservoir 32 can be configured in a wide variety of sizes and shapes. For percutaneous implantation, the shrink polymer reservoir 32 can be shaped in as a narrow tube to facilitate insertion into a body. The shrink polymer reservoir is typically manufactured from a shrink polymer that is therapeutic substance compatible and biocompatible. In some embodiments, the shrink polymer reservoir 32 can also include a safety reservoir 90 to contain therapeutic substance 26 dispensed by the shrink polymer reservoir 32 that has not yet passed through the flow restriction 88. In some embodiments, the shrink polymer therapeutic substance delivery device 86 can also include a capsule 92 covering the shrink polymer reservoir 32. The capsule 92 can be made permeable to gas and body fluids, so the gas and body fluids migrate into the capsule as the reservoir 32 collapses to maintain a substantially constant internal pressure within the capsule. The capsule 92 can provide a uniform shape for the shrink polymer reservoir 32 to facilitate implantation and explanation in a body.

The flow restriction 88 is fluidly coupled to the reservoir outlet 36 to receive therapeutic substance 26 dispensed from the reservoir 32 at the reservoir rate. The flow restriction 88 is configured to control the reservoir rate to an infusion rate. The flow restriction 88 operates as a means for restricting flow that is fluidly coupled to the means for containing to restrict therapeutic substance 26 flow from the means for containing to a therapeutic substance infusion rate. The flow restriction 88 can be a fixed rate flow restriction such as a capillary tube, a precision orifice, and the like. The flow restriction 88 can also be a variable rate flow restriction such as the MEMS flow restrictor 34 discussed previously. The shrink polymer therapeutic substance delivery device 86 can also include a check valve 94 coupled to the reservoir outlet 36. The check valve 94 is used to reduce the opportunity for unintended therapeutic substance infusion.

Figure 12:
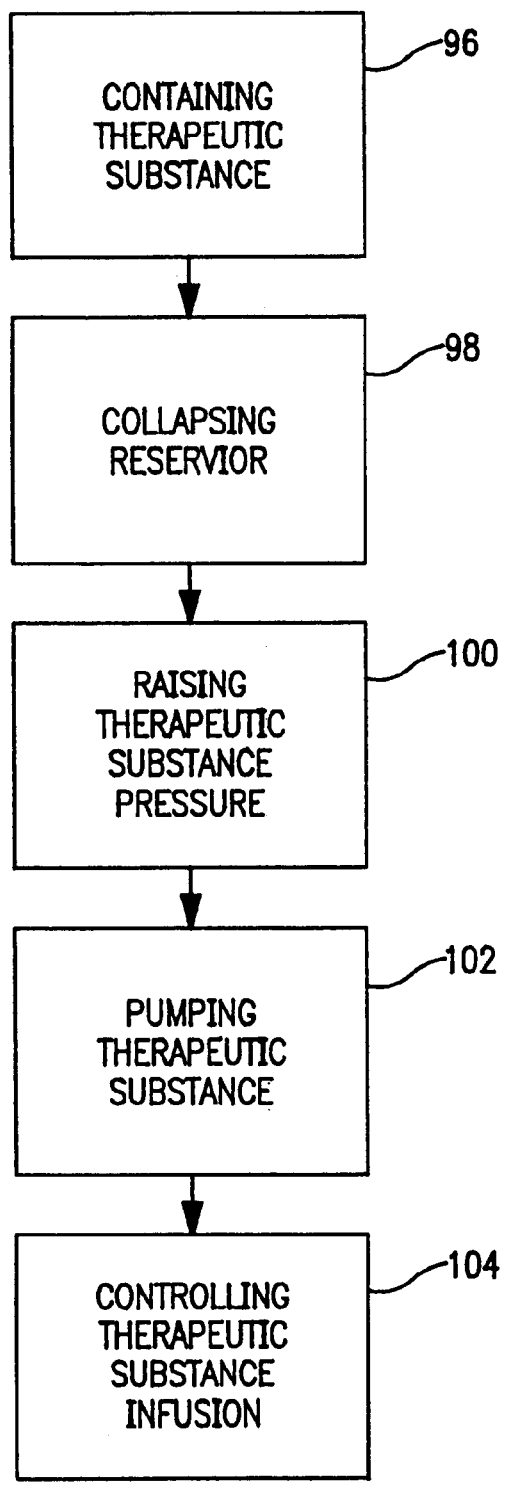

FIG. 12 shows a method for delivering a therapeutic substance from a shrink polymer reservoir 32 with infusion rate control. The method comprises the following elements. Therapeutic substance 26 is contained 96 in a shrink polymer reservoir 32 having a reservoir outlet 36. The shrink polymer reservoir 32 is collapsed 98 in a controlled manner. Therapeutic substance pressure contained in the shrink polymer reservoir 32 is raised 100. Therapeutic substance 26 is pumped 102 from the shrink polymer reservoir 32 through the reservoir outlet 36 and into a flow restriction 88. Therapeutic substance 26 that flows from the reservoir outlet 36 is controlled 104 with the flow restriction 88 to an infusion rate. Therapeutic substance 26 is infused at the infusion rate. The method can also include delivering therapeutic substance through a catheter 22 to a therapeutic substance infusion site. The method can also include implanting the shrink polymer reservoir with infusion control into a patient.

Thus, embodiments of the single-use therapeutic substance delivery device with infusion rate control are disclosed that are versatile, relatively inexpensive, relatively small, and provide many other improvements. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A single-use therapeutic substance delivery device with infusion rate control, comprising:
    a single-use reservoir configured for controlled collapsing to dispense therapeutic substance from the reservoir at a reservoir rate through a reservoir outlet; and,
    a Micro Electro Mechanical System (MEMS) flow restriction fluidly coupled to the reservoir outlet to receive therapeutic substance dispensed from the reservoir at the reservoir rate and restrict the therapeutic substance flow to an infusion rate.

2. The single-use therapeutic substance delivery device as in claim 1 wherein the single-use therapeutic substance delivery device is configured to be implanted into a patient.

3. The single-use therapeutic substance delivery device as in claim 2 wherein the single-use therapeutic substance delivery device is configured to be percutaneously inserted into a patient.

4. The single-use therapeutic substance delivery device as in claim 2 wherein the single-use therapeutic substance delivery device is configured to be programmed after implantation.

5. The single-use therapeutic substance delivery device as in claim 1 wherein the single-use reservoir is a shrink polymer reservoir.

6. The single-use therapeutic substance delivery device as in claim 1 wherein the single-use reservoir is an elastomeric bladder.

7. A shrink polymer therapeutic substance delivery device with infusion rate control, comprising:
    a shrink polymer reservoir configured for controlled collapsing to dispense therapeutic substance from the reservoir at a reservoir rate through a reservoir outlet; and,
    a flow restriction fluidly coupled to the reservoir outlet to receive therapeutic substance dispensed from the reservoir at the reservoir rate and restrict the therapeutic substance flow to an infusion rate.

8. The shrink polymer therapeutic substance delivery device as in claim 7, further comprising a catheter coupled to the flow restriction, the catheter adapted to be implanted and deliver therapeutic substance to a delivery site at the infusion rate.

9. The shrink polymer therapeutic substance delivery device as in claim 7 wherein the shrink polymer therapeutic substance delivery device is configured to be implanted.

10. The shrink polymer therapeutic substance delivery device as in claim 9 wherein the shrink polymer therapeutic substance delivery device is configured to be percutaneously inserted into a patient.

11. The shrink polymer therapeutic substance delivery device as in claim 9 wherein the shrink polymer therapeutic substance delivery device is configured to be programmed after implantation.

12. The shrink polymer therapeutic substance delivery device as in claim 7, further comprising a safety reservoir to contain therapeutic substance dispensed by the shrink polymer reservoir that has not yet passed through the flow restriction.

13. The shrink polymer therapeutic substance delivery device with as in claim 7, further comprising a capsule containing the shrink polymer reservoir, the capsule being permeable to gas and body fluids, so the gas and body fluids migrate into the capsule as the reservoir collapses to maintain a substantially constant internal pressure within the capsule.

14. The shrink polymer therapeutic substance delivery device as in claim 7 further comprising a check valve coupled to the reservoir outlet.

15. The shrink polymer therapeutic substance delivery device as in claim 7 wherein the flow restriction is a fixed rate flow restriction.

16. The shrink polymer therapeutic substance delivery device as in claim 15 wherein the fixed rate flow restriction is selected from the group consisting of a capillary tube and a precision orifice.

17. The shrink polymer therapeutic substance delivery device as in claim 7 wherein the flow restriction is a variable rate flow restriction.

18. The shrink polymer therapeutic substance delivery device as in claim 17 wherein the variable rate flow restriction is selected from the group consisting of a Micro Electro Mechanical System (MEMS), and a mechanically adjustable flow restriction.

19. A single-use therapeutic substance delivery device with infusion rate control, comprising:

means for containing a therapeutic substance that collapses in a controlled manner to dispense therapeutic substance from the means for containing;

means for restricting flow to restrict therapeutic substance flow from the means for containing to a therapeutic substance infusion rate; and, means for delivering therapeutic substance to delivery therapeutic substance at the therapeutic substance infusion rate to a therapeutic substance infusion site.

20. A method for delivering a therapeutic substance from single-use reservoir with infusion rate control, comprising:

containing a therapeutic substance in a single-use reservoir having an reservoir outlet;

collapsing in a controlled manner the single-use reservoir;

raising therapeutic substance pressure contained in the single-use reservoir;

pumping therapeutic substance from the single-use reservoir through the reservoir outlet and into a flow restriction;

controlling therapeutic substance flow from the reservoir outlet with the flow restriction to an infusion rate; and, infusing therapeutic substance at the infusion rate.

21. The method as in claim 20, further comprising delivering therapeutic substance through a catheter to a therapeutic substance infusion site.

22. The method as in claim 20, further comprising implanting the single-use reservoir with infusion control into a patient.

23. The method as in claim 20 wherein the single-use reservoir is a shrink polymer reservoir.

24. The method as in claim 20 wherein the single-use reservoir is an elastomeric diaphragm.

25. A Micro Electo Mechanical System (MEMS) variable flow restriction for a single-use therapeutic substance delivery device, comprising:

a substrate having a therapeutic substance flow path with a drug input, a flow restriction, and a therapeutic substance output;

a passive power source carried on the substrate, the passive power source capable of supplying power upon being energized by a radio frequency source;

electronics carried on the substrate and coupled to the passive power supply, the electronics generating a control signal;.

an actuator carried on the substrate and coupled to the electronics, the actuator moving in response to the control signal; and, a valve movably coupled to the substrate to selectively engage the flow restriction, the valve operated by the actuator to selectively adjust the flow restriction to an infusion rate.

26. The MEMS flow restrictor as in claim 25 wherein the electronics include nonvolatile memory.

27. The MEMS flow restrictor as in claim 25 wherein the actuator is a Direct Current (DC) motor coupled to the valve with a gear.

28. The MEMS flow restrictor as in claim 25 wherein the actuator is a heat motor coupled to the valve with a ratchet wheel.

29. The MEMS flow restrictor as in claim 25 wherein the actuator is a stepwise rotor coupled to the valve.

30. The MEMS flow restrictor as in claim 25 wherein the flow restriction is a continuous path.

31. The MEMS flow restrictor as in claim 25 wherein the flow restriction is a plurality of restriction outlets selectable by the valve.

32. The MEMS flow restrictor as in claim 25 further comprising a single-use therapeutic substance reservoir coupled to the MEMS flow restrictor.

33. The MEMS flow restrictor as in claim 32 wherein the single-use therapeutic substance reservoir is a shrink-polymer reservoir.

34. The MEMS flow restrictor as in claim 32 wherein the single-use therapeutic substance reservoir is an elastomeric bladder.

35. A Micro Electo Mechanical System (MEMS) flow restriction for a therapeutic substance delivery device with infusion rate control, comprising:

means for therapeutic substance flow having a therapeutic substance input, a flow restriction, and a therapeutic substance output;

means for power carried on the means for therapeutic substance flow, the means for power capable of supplying power upon being energized by a radio frequency source;

means for programming to store flow restriction program;

means for electronics to receive the flow restriction program and generate a control signal;

means for actuation to create motion in response to the control signal; and, means for valuing to adjust therapeutic substance flow through the flow restriction upon operation of the means for actuation.

36. A method for operating a Micro Electro Mechanical System (MEMS) therapeutic substance flow restriction, comprising:

energizing a passive power supply with a radio frequency signal;

powering electronics with the passive power supply;

receiving an information signal modulated on the radio frequency signal with the electronics;

generating a control signal that is responsive to the information signal with the electronics;

operating an actuator in response to the control signal; and, adjusting the valve to adjust the flow restriction to an infusion rate.

37. The method as in claim 36, further comprising transmitting a status signal with the electronics.

* * * * *